United States Patent
Marciano et al.

(10) Patent No.: US 12,333,713 B2
(45) Date of Patent: Jun. 17, 2025

(54) METHODS AND APPARATUSES FOR DETERMINING TRANSDUCER LOCATIONS TO GENERATE TUMOR TREATING FIELDS

(71) Applicant: Novocure GmbH, Root (CH)

(72) Inventors: Tal Marciano, Haifa (IL); Oshrit Zeevi, Haifa (IL)

(73) Assignee: Novocure GmbH, Baar (CH)

( * ) Notice: Subject to any disclaimer, the term of this patent is extended or adjusted under 35 U.S.C. 154(b) by 591 days.

(21) Appl. No.: 17/517,407

(22) Filed: Nov. 2, 2021

(65) Prior Publication Data

US 2022/0148171 A1    May 12, 2022

Related U.S. Application Data

(60) Provisional application No. 63/110,674, filed on Nov. 6, 2020.

(51) Int. Cl.
*G06T 7/00* (2017.01)
*G06V 10/44* (2022.01)

(52) U.S. Cl.
CPC ............ *G06T 7/0012* (2013.01); *G06V 10/44* (2022.01); *G06T 2207/30008* (2013.01);
(Continued)

(58) Field of Classification Search
CPC ......... G06T 7/0012; G06T 2207/30008; G06T 2207/30096; G06T 2207/30172;
(Continued)

(56) References Cited

U.S. PATENT DOCUMENTS

| 7,565,205 B2 | 7/2009 | Palti | |
|---|---|---|---|
| 2014/0148679 A1* | 5/2014 | Eary | G06T 7/0012 |
| | | | 600/407 |

(Continued)

FOREIGN PATENT DOCUMENTS

CN    111603688 A    9/2020

OTHER PUBLICATIONS

Chaudhry, A., Benson, L., Varshaver, M., Farber, O., Weinberg, U., Kirson, E. and Palti, Y., 2015. NovoTTF™-100A System (Tumor Treating Fields) transducer array layout planning for glioblastoma: a NovoTAL™ system user study.*

*Primary Examiner* — Zhitong Chen
(74) *Attorney, Agent, or Firm* — McCarter & English, LLP; Michael A. Sartori

(57) ABSTRACT

A computer-implemented method to determine placement of transducers on a subject's body, the method including: selecting a plurality of intersecting line segment pairs on an image of the subject's body, each of the line segment pairs intersecting in a region of the image corresponding to a tumor in the subject's body, each of the line segment pairs corresponding to locations to place the transducers on the subject's body; determining a pair value for each of the intersecting line segment pairs, each pair value based on a length of each line segment of the corresponding intersecting line segment pair; selecting one or more intersecting line segment pairs based on the pair values to obtain one or more selected intersecting line segment pairs; and outputting the locations to place the transducers on the subject's body corresponding to the one or more selected intersecting line segment pairs.

19 Claims, 5 Drawing Sheets

(52) U.S. Cl.
CPC ............... *G06T 2207/30096* (2013.01); *G06T 2207/30172* (2013.01); *G06V 2201/03* (2022.01)

(58) Field of Classification Search
CPC . G06T 2207/10081; G06T 2207/10116; G06T 7/60; G06T 2207/10088; G06T 2207/30016; G06V 10/44; G06V 2201/03; G06V 10/751; G16H 20/40; G16H 30/40; G16H 40/63; G16H 50/50; G16H 20/30; A61N 1/40; A61N 1/3603; A61N 1/403; A61N 1/36002; A61N 1/0476

See application file for complete search history.

(56) References Cited

U.S. PATENT DOCUMENTS

| | | |
|---|---|---|
| 2016/0346536 A1* | 12/2016 | Palti .................. A61N 1/32 |
| 2017/0120041 A1 | 5/2017 | Wenger et al. |
| 2018/0160933 A1 | 6/2018 | Urman et al. |
| 2019/0314631 A1 | 10/2019 | Wong et al. |
| 2020/0146586 A1 | 5/2020 | Naveh et al. |

* cited by examiner

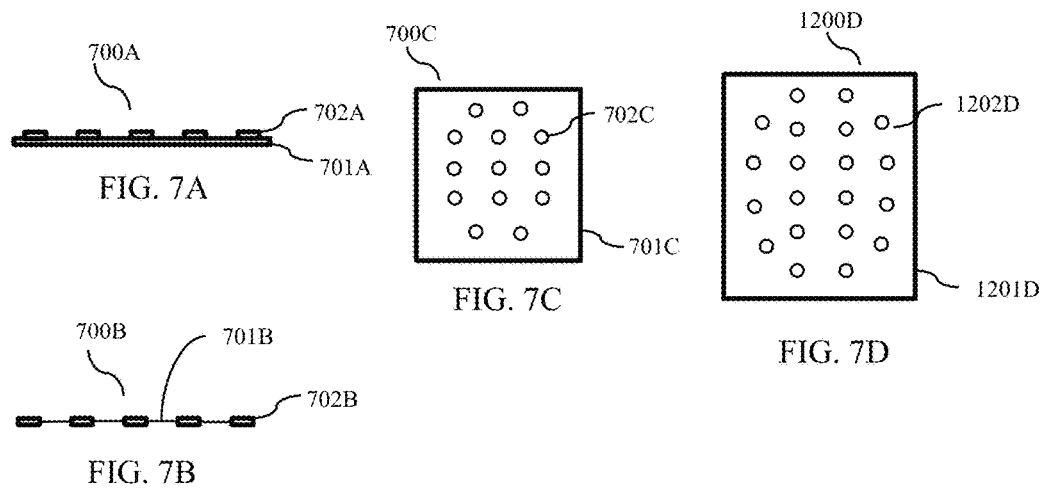
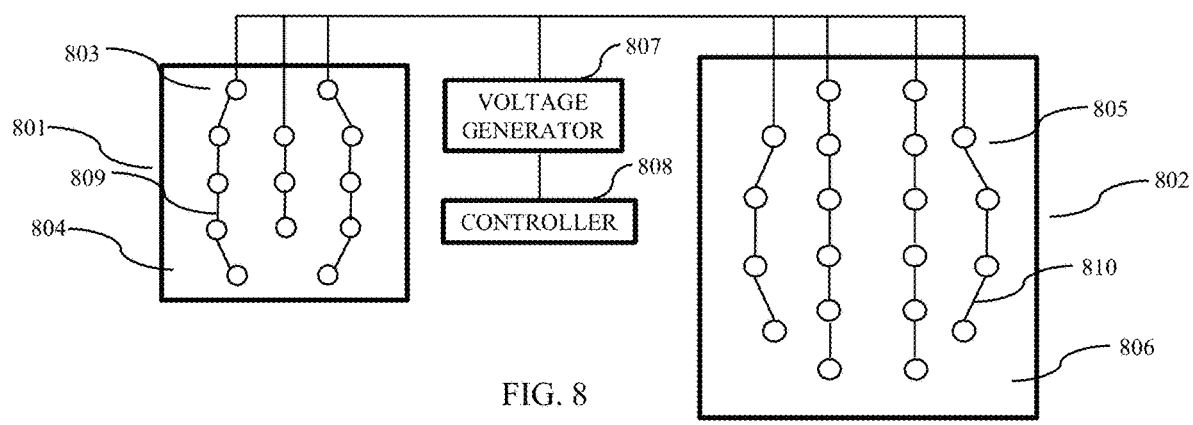
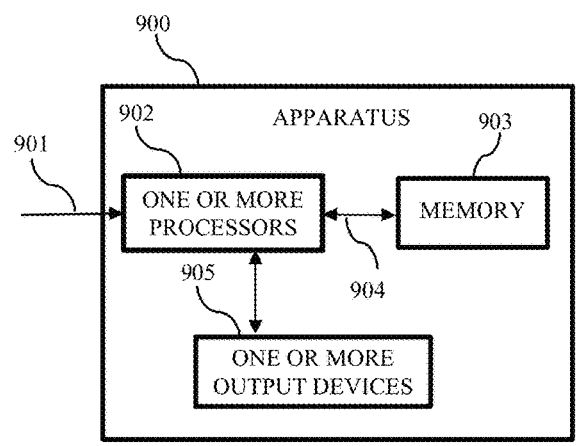

US 12,333,713 B2

METHODS AND APPARATUSES FOR DETERMINING TRANSDUCER LOCATIONS TO GENERATE TUMOR TREATING FIELDS

CROSS-REFERENCE TO RELATED APPLICATIONS

This application claims priority to U.S. Patent Application No. 63/110,674 filed on Nov. 6, 2020, which is incorporated herein by reference.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into a region of interest by transducers placed on the patient's body and applying AC voltages between the transducers. Conventionally, a first pair of transducers and a second pair of transducers are placed on the subject's body. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

SUMMARY OF THE INVENTION

One aspect of the invention is directed to a computer-implemented method of determining placement of transducers on a subject's body. The computer includes one or more processors and memory accessible by the one or more processors, the memory storing instructions that when executed by the one or more processors cause the computer to perform the method. The method includes selecting a plurality of intersecting line segment pairs on an image of the subject's body, each of the line segment pairs intersecting in a region of the image corresponding to a tumor in the subject's body, each of the line segment pairs corresponding to locations to place the transducers on the subject's body; determining a pair value for each of the intersecting line segment pairs, each pair value based on a length of each line segment of the corresponding intersecting line segment pair; selecting one or more intersecting line segment pairs based on the pair values to obtain one or more selected intersecting line segment pairs; and outputting the locations to place the transducers on the subject's body corresponding to the one or more selected intersecting line segment pairs.

The above aspect of the invention is exemplary, and other aspects and variations of the invention will be apparent from the following detailed description of embodiments.

BRIEF DESCRIPTION OF THE DRAWINGS

FIGS. 7A-7D illustrate examples of the structure of various transducers.

FIG. 8 illustrates an example of a configuration of a pair of transducers.

FIG. 9 illustrates an example of an apparatus to determine placement of transducers on a subject's body.

DESCRIPTION OF EMBODIMENTS

To provide a subject with the an effective TTFields treatment, precise locations at which to place the transducers on the subject's body must be generated, and these precise locations are based on the type of cancer and the location of the cancer in the subject's body. However, determining these precise locations is very challenging and involves lengthy and resource intensive computer simulations of numerous possible locations to place the transducers.

One difficulty in these computer simulations is to account for the conductivities of the different types of tissue (e.g., bone, organs, fluid, skin, and tumor) in the computer simulations. A further difficulty is in modeling higher resolution images for computer simulations, resulting in more complex computer models of the subject's body. As a result, detailed computer simulations of the subject's body for numerous possible locations of the transducers are very costly in terms of computational resources and time.

The inventors recognized these problems and discovered an approach to determine precise locations at which to place the transducers on the subject's body without costly simulations. In particular, the positions at which to place transducers on a subject's body may be determined based on relationships between the transducers used to induce TTFields. The relationships between the transducers may be based on, for example, the distance between the transducers, the pixels between the transducers in an image of the subject's body, and/or the tissue between the transducers in an image of the subject's body.

Figure 1:
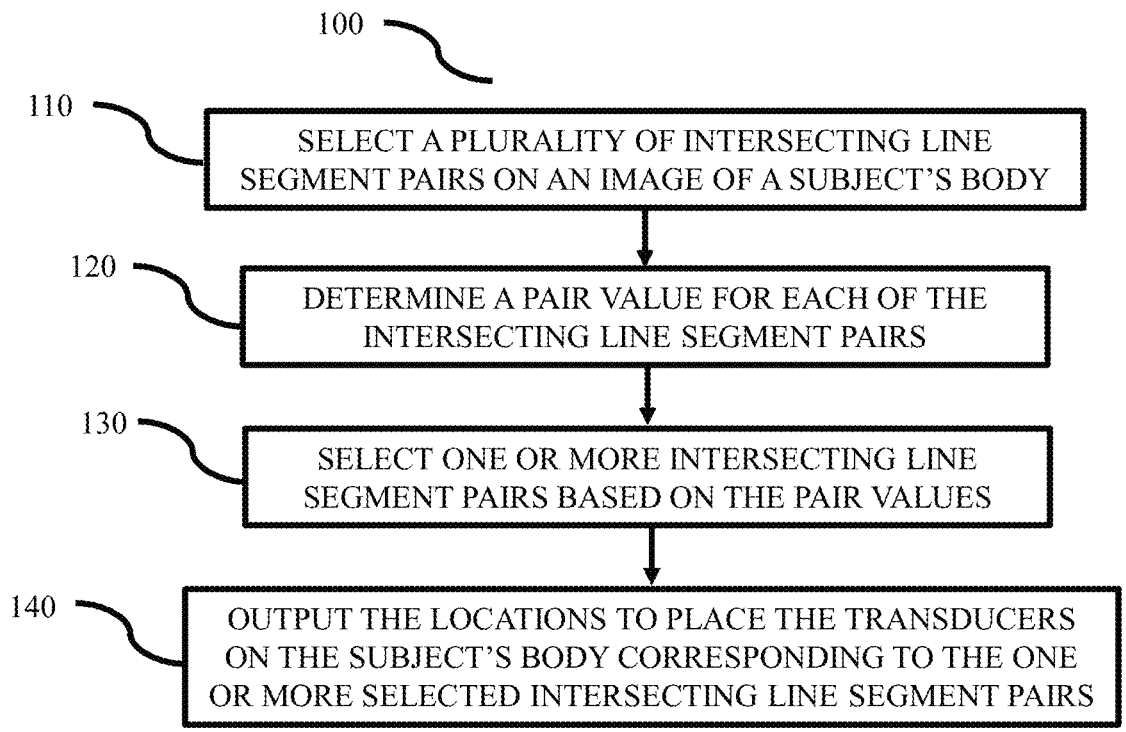
FIG. 1 is a flowchart depicting an example of determining placement of transducers on a subject's body.

FIG. 1 is a flowchart depicting an example of determining placement of transducers on a subject's body. In one embodiment, each transducer may be an array of electrode elements, and each line segment may thus represent a distance between center points of a pair of transducer arrays.

At step 110, the method 100 may select a plurality of intersecting line segment pairs on an image of the subject's body. In one embodiment, each intersecting line segment pair may have a first line segment and a second line segment. The image of the subject's body may include a region associated with a tumor in the subject's body. The image of the subject's body may, for example, be an X-ray image, a computerized tomography (CT) image, a magnetic resonance imaging (MRI) image, or an ultrasound image of the subject's body, or any image of the subject's body providing an internal view of the subject's body. The image may be a so-called slice through the subject's body obtained by scanning equipment.

Each line segment of each intersecting line segment pair may identify locations to place a pair of transducers on the subject's body. Each pair of transducers may correspond to a channel for generating TTFields in the subject's body. A particular line segment may be used in only one or more than one intersecting line segment pair. Each intersecting line segment pair intersects in a region corresponding to a tumor in the subject's body.

Each line segment may represent a distance between two transducers and may be defined by, for example, a point on a first transducer and a point on a second transducer, an intersection with the first transducer and an intersection with the second transducer, pixels of the image, and/or voxels of the image.

Each line segment of the pair of intersecting line segments may intersect at an intersection angle in the region of the image corresponding to the tumor in the subject's body. For example, the line segment pair may intersect within the tumor in the image, at a centroid of the tumor in the image, or at a point adjacent to the tumor in the image. The line segments of each intersecting line segment pair may be substantially perpendicular, intersect at an angle based on the physical geometry of the subject's body, or intersect at an angle based on the type of transducer to be used on the subject's body. In some cases, an intersection angle within 90°±15° may be required.

At step 120, the method 100 may determine a pair value for each of the intersecting representative line segment pairs. In one embodiment, the pair value may be based on a length of each line segment of the corresponding intersecting line segment pair. In one example, the pair value of the intersecting representative line segment pair may be calculated, for example, as an absolute value of a difference between the lengths of the line segments in the intersecting line segment pair. In another example, the pair value of the intersecting representative line segment pair may be calculated as a summation of the lengths of the line segments in the intersecting line segment pair.

In one embodiment, the length of each representative line segment may be calculated based on a distance (e.g. mm) between the endpoints of the representative line segment in the image, a geometric distance (e.g., mm) of each representative line segment, or the relative units of the image. In one example, the pair value T of the intersecting representative line segment pair may be calculated by the following equation:

$$T = |d1 - d2| \qquad \text{Equation 1}$$

where d1 and d2 are the distances of the first line segment and the second line segment of the intersecting representative line segment pair.

In another example, the pair value T for each intersecting representative line segment pair may be calculated by the following equation:

$$T = d1 + d2 \qquad \text{Equation 2}$$

where d1 and d2 are the distances of the first line segment and the second line segment of the intersecting representative line segment pair.

In another embodiment, the length of each representative line segment may be calculated based on a number of pixels or a number of voxels in the image between the endpoints of the representative line segment. In a more specific example, the method may identify pixels of the image with which each line segment of each of the intersecting line segment pairs intersects. In another example, the method further comprises assigning pixel tissue values to pixels of the image based on tissue types of the subject's body and determining the pair value based on the pixel tissue values for the pixels intersecting each line segment of the intersecting line segment pair.

In one example, the pair value T for each intersecting representative line segment pair may be calculated by the following equation:

$$T = |d1 - d2| = |\Sigma_p^{N_1} d1_p - \Sigma_v^{N_2} d2_v| \qquad \text{Equation 3}$$

where the first line segment of the intersecting line segment pair has $N_1$ pixels $d1_p$ and the second line segment of the intersecting line segment pair has $N_2$ pixels $d2_v$.

In another example, the pair value T for each intersecting representative line segment pair may be calculated by the following equation:

$$T = d1 + d2 = \Sigma_p^{N_1} d1_p + \Sigma_v^{N_2} d2_v \qquad \text{Equation 4}$$

where the first line segment of the intersecting line segment pair has $N_1$ pixels $d1_p$ and the second line segment of the intersecting line segment pair has $N_2$ pixels $d2_v$.

In another embodiment, each pair value may be based on the weighted distance between the first endpoint and the second endpoint of each line segment of the corresponding intersecting line segment pair. In one example, the weighted distance between the first endpoint and the second endpoint of each line segment is based on one or more tissue types within the portion of the subject's body through which the corresponding line segment passes. In a more specific example, the method further comprises assigning pixel tissue weightings to pixels of the image of the subject's body based on tissue types of the subject's body. In one example, the tissue types of the subject's body comprise gray matter, white matter, and bone. In another example, the tissue types of the subject's body comprise organ tissue, muscular tissue, and bone. The weight may be based on, for example, the tissue type conductivity or resistivity.

In one example, the pair value T for each intersecting representative line segment pair may be calculated by the following equation:

$$T = |d1 - d2| = |\Sigma_p^{N_1} w1_p d1_p - \Sigma_v^{N_2} w2_v d2_v| \qquad \text{Equation 5}$$

where the first line segment of the intersecting line segment pair has $N_1$ pixels $d1_p$, the second line segment of the intersecting line segment pair has $N_2$ pixels $d2_v$, the pixel $d1_p$ has a tissue weight $w1_p$, and the pixel $d2_v$ has a tissue weight $w2_v$.

In another example, the pair value T for each intersecting representative line segment pair may be calculated by the following equation:

$$T = d1 + d2 = \Sigma_p^{N_1} w1_p d1_p + \Sigma_v^{N_2} w2_v d2_v \qquad \text{Equation 6}$$

where the first line segment of the intersecting line segment pair has $N_1$ pixels $d1_p$, the second line segment of the intersecting line segment pair has $N_2$ pixels $d2_v$, the pixel $d1_p$ has a tissue weight $w1_p$, and the pixel $d2_v$ has a tissue weight $w2_v$.

At step 130, the method 100 may select one or more intersecting representative line segment pairs based on the pair values determined at step 120. For example, if an absolute value calculation is used to determine the pair values, the pair values may be sorted, the smaller pair values or the smallest pair value may be determined, and the intersecting representative line segment pairs corresponding to the smaller pair values or the smallest pair value may be selected. As another example, if a summation calculation is used to determine the pair values, the pair values may be sorted, the smaller pair values or the smallest pair value may be determined, and the intersecting representative line segment pairs corresponding to the smaller pair values or the smallest pair value may be selected.

As another example, the intersecting representative line segment pairs may be selected based on comparing a threshold to the pair values of the intersecting line segment pairs. For example, if an absolute value calculation is used to determine the pair values, the intersecting line representative segment pairs corresponding to pair values at or below the threshold may be selected. As another example, if a summation calculation is used to determine the pair values, the intersecting representative line segment pairs corresponding to pair values at or below the threshold may be selected.

In one embodiment, at least one of the one or more selected intersecting representative line segment pairs may have a local minimum power density (LMiPD) at an intersection of the line segments that is higher than an LMiPD at an intersection of the line segments of non-selected intersecting line segment pairs. The LMiPD may represent the minimum dose delivered by the TTFields to the tumor via a particular transducer layout, and an ideal transducer layout may be obtained when this minimum dose is maximized relative to other potential layouts.

In another embodiment, the one or more selected intersecting line segment pairs are selected without simulating TTFields for transducer locations on the subject's body.

At step 140, the method 100 may output the locations to place the transducers on the subject's body corresponding to the one or more selected intersecting representative line segment pairs. The output may be sent to a user device. In one embodiment, the locations to place the transducers on the subject's body are outputted without simulating the TTFields for the locations.

Figure 2:
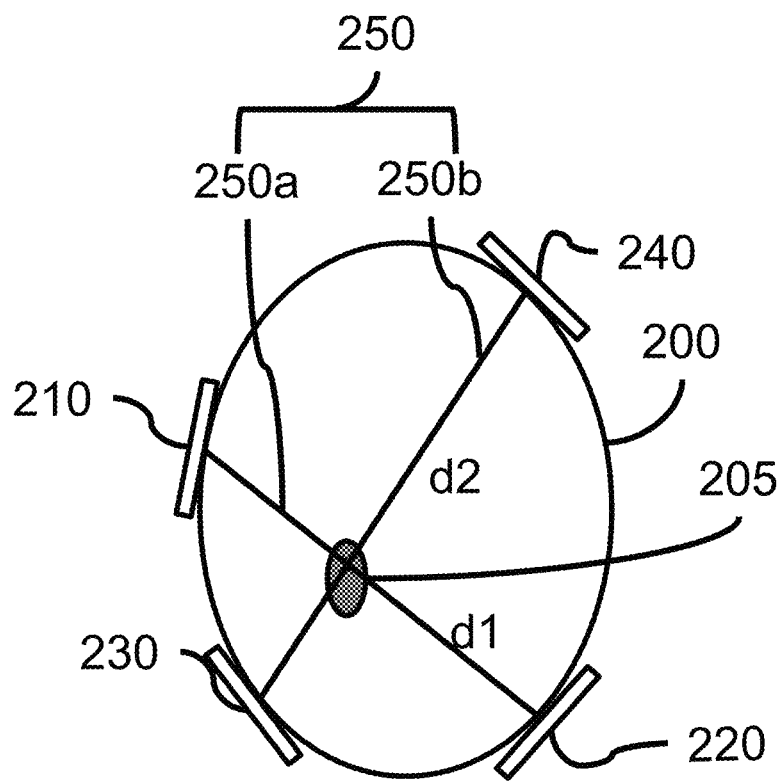
FIG. 2 illustrates an example of a subject's body in which an intersecting line segment pair passes through a tumor.

FIG. 2 illustrates an example portion of a subject's body in which an intersecting line segment pair passes through a tumor. In the example depicted in FIG. 2, the image 200 of the subject's body includes a tumor 205, and a first line segment 250a and a second line segment 250b intersecting in the tumor 205. The first line segment 250a corresponds to the locations of a first transducer 210 and a second transducer 220. In one example, the endpoints of the first line segment 250a may correspond to the locations of the centers of the transducers 210 and 220. The second line segment 250b corresponds to the locations of a third transducer 230 and a fourth transducer 240. In one example, the endpoints of the second line segment 250b may correspond to the locations of the centers of the transducers 230 and 240. The first line segment 250a and the second line segment 250b form an intersecting line pair 250. The first line segment 250a and the second line segment 250b intersect at substantially 90°.

The line segment 250a may have a length between the first transducer 210 and the second transducer 220 represented by distance (or length) d1, and line segment 250b may have a length between the third transducer 230 and the fourth transducer 240 represented by distance (or length) d2. In one embodiment, the pair value of the intersecting line pair 250 may be calculated based on Equations 1-4 discussed above.

Figure 3:
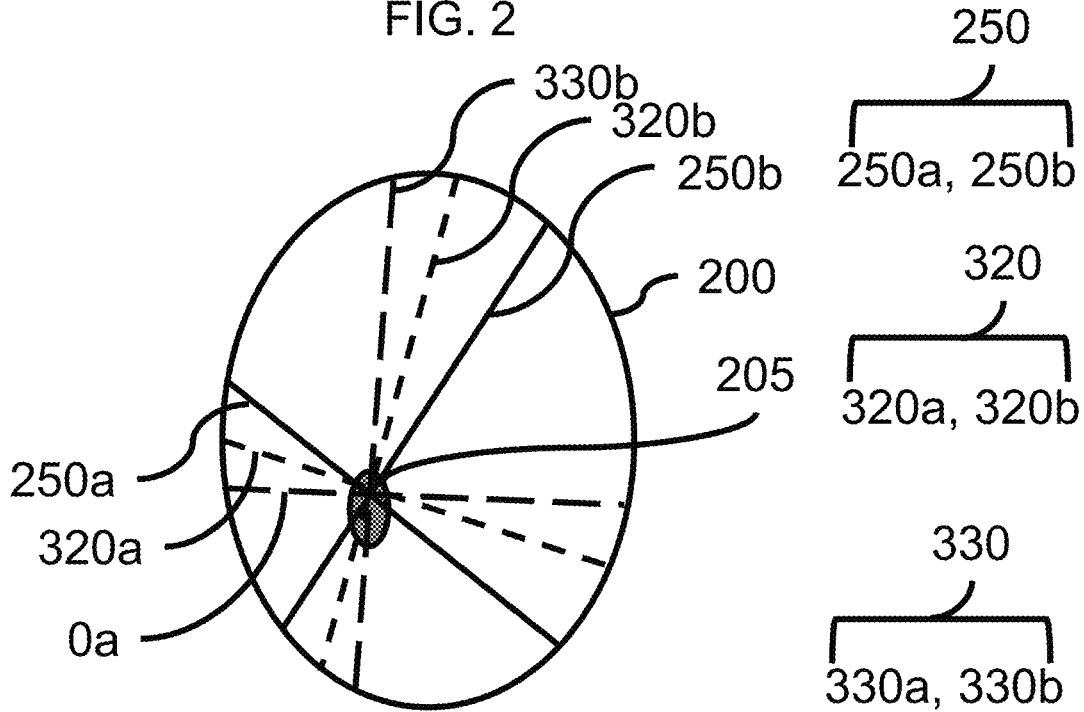
FIG. 3 illustrates an example of a subject's body in which intersecting line segment pairs pass through a tumor.

FIG. 3 illustrates an example portion of a subject's body in which intersecting line segment pairs pass through a tumor. In the example depicted in FIG. 3, the image 200 of the subject's body includes three intersecting line segment pairs representing the locations of three pairs of transducers. For clarity, the three pairs of transducers are not shown in FIG. 3. In particular, the image 200 of the subject's body includes the first intersecting line segment pair 250 of the line segments 250a and 250b, a second intersecting line segment pair 320 of line segments 320a and 320b, and a third intersecting line segment pair 330 of line segments 330a and 330b. Each of the intersecting line segment pairs intersects within the tumor 205.

Potential transducer locations on the subject's body may be spaced apart by predetermined angles. As an example, the first line segments of each intersecting representative line segment pair may be spaced apart by a predetermined angle, and the second line segments of each intersecting line segment pair may be spaced apart by the predetermined angle. The predetermined angle may be, for example, 0.5°, 1°, 5°, 10°, 15°, 30°, 45°, 60°, 90°, or any other angle. As another example, the line segments of each intersecting line segment pair may be spaced apart by different angles. In the example depicted in FIG. 3, the first line segment 250a of the first intersecting line segment pair 250 may be spaced apart by a predetermined angle from the first line segment 320a of the second intersecting line segment pair 320, and the first line segment 320a of the second intersecting line segment pair 320 may be spaced apart by the predetermined angle from the first line segment 330a of the third intersecting line segment pair 330. Similarly, the second line segment 250b of the first intersecting line segment pair 250 may be spaced apart by the predetermined angle from the second line segment 320b of the second intersecting line segment pair 320, and the second line segment 320b of the second intersecting line segment pair 320 may be spaced apart by the predetermined angle from the second line segment 330b of the third intersecting line segment pair 330.

Figure 4:
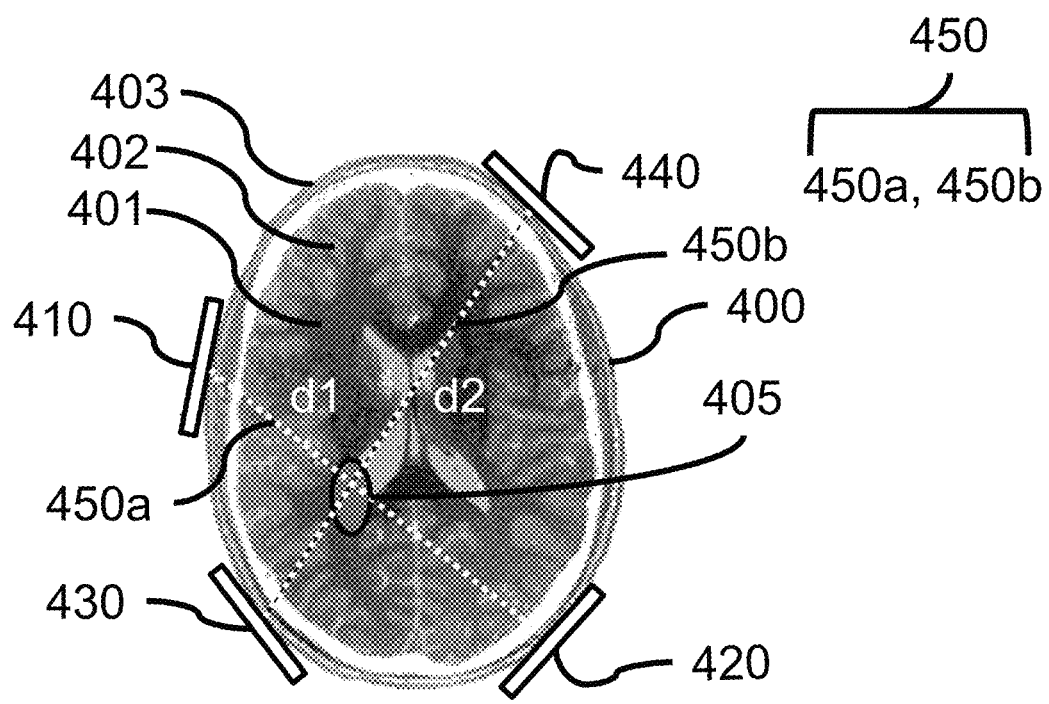
FIG. 4 illustrates an example magnetic resonance imaging (MRI) image of a subject's head in which an intersecting line segment pair passes through different tissue types and a tumor.

FIG. 4 illustrates an example magnetic resonance imaging (MRI) image of a subject's head in which an intersecting line segment pair passes through different tissue types and a tumor. In the example depicted in FIG. 4, MRI image 400 of a subject's head includes a tumor 405, an intersecting representative line segment pair 450 passes through different tissue types and intersects with the tumor 405. The intersecting representative line segment pair 450 includes a first line segment 450a and a second line segment 450b. The first line segment 450a is defined by the locations of the transducers 410 and 420, and the second line segment 450b is defined by the locations of the transducers 430 and 440. The tissue types of the subject's body may include gray matter 401, white matter 402, bone 403, brain fluid, and skin. In FIG. 4, the first line segment 450a and the second line segment pass through multiple tissue types (e.g., skin, bone, brain fluid, white matter, and/or gray matter). The distance d1 of line segment 450a may include multiple pixels passing through skin, bone, brain fluid, white matter, and gray matter, with each pixel being weighted accordingly. Then, d1 may be the summation of each weighted pixel along the line segment 450a. Similarly, the distance d2 of line segment 450b may be the summation of each weighted pixel along the line segment 450b. The pair value of the intersecting line pair 450 may be calculated based on Equations 5-6 discussed above.

Figure 5:
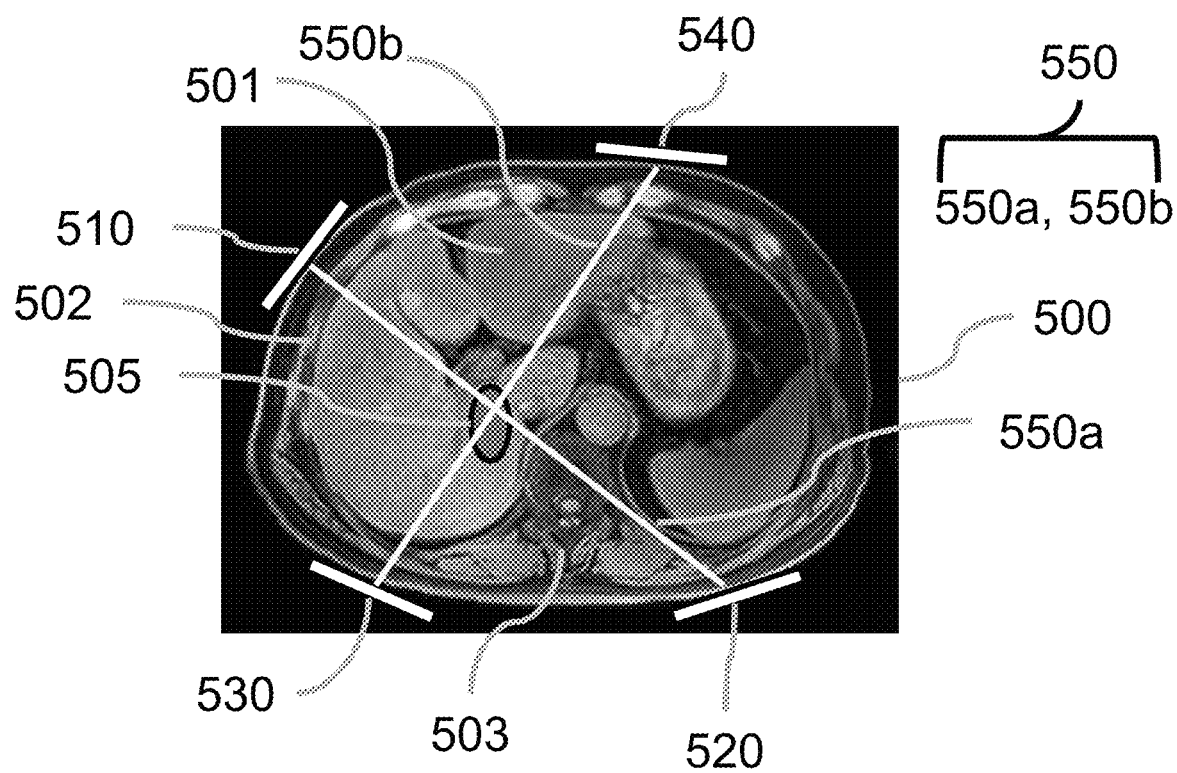
FIG. 5 illustrates an example MRI image of a subject's torso in which an intersecting line segment pair passes through different tissue types and a tumor.

FIG. 5 illustrates an example MRI image of a subject's torso in which an intersecting line segment pair passes through different tissue types and a tumor. In the example depicted in FIG. 5, the MRI image 500 of the subject's torso includes a tumor 505 and an intersecting representative line segment pair 550 passing through different tissue types and intersecting with the tumor 505. The tissue types of the subject's body may include organ tissue 501, muscular tissue 502, bone 503, skin, and fluid. The intersecting representative line segment pair 550 includes a first line segment 550a and a second line segment 550b. The first line segment 550a is defined by the locations of the transducers 510 and 520, and the second line segment 550b is defined by the locations of the transducers 530 and 540.

Figure 6A:
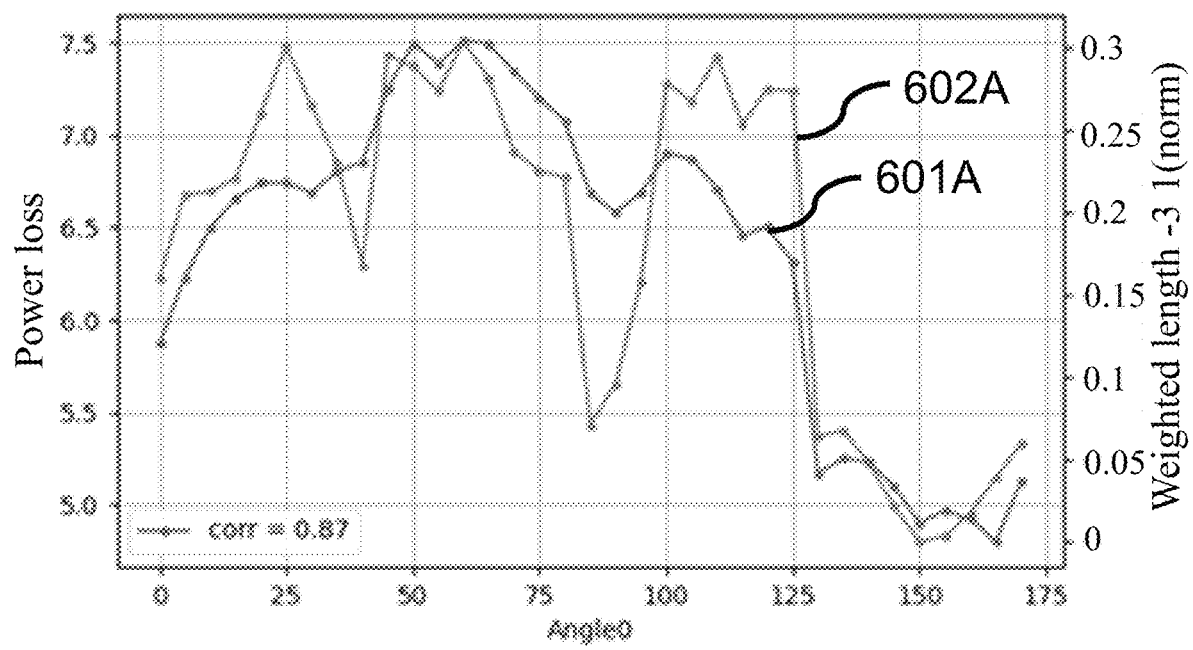
FIGS. 6A and 6B illustrate example graphs comparing a calculation of the LMiPD to exemplary embodiments of the invention.
Figure 6B:
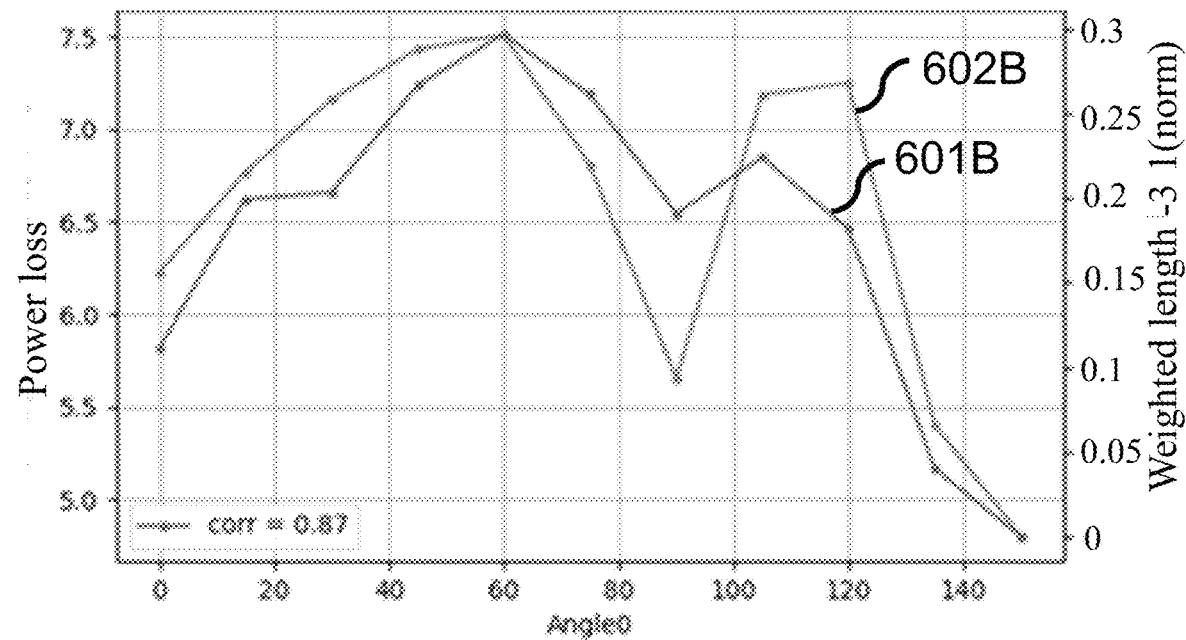

FIGS. 6A and 6B illustrate example graphs comparing a calculation of the local minimum power density (LMiPD) to exemplary embodiments of the invention.

In FIGS. 6A and 6B, the x-axis corresponds to angles of a channel (CH0) for a pair of transducers on a subject's head, where 0° refers to the front-back line of the subject's head and where the angles are with respect to this front-back line, the left y-axis corresponds to power loss units (mW/cm$^3$), and the right y-axis corresponds to normalized weighted distance between the pair of transducers. In one example, a weight w with a relative value between −3 and 3 may be assigned to a pixel based on its respective tissue type. The graph includes the power loss for the channel (CH0) for the pair of transducers positioned in a front-to-back orientation on the subject's head and then shifted by the angle of the x-axis. The angles for the data points of the channel (CH0) are between 0° and 170° in 5° increments.

In the example depicted in FIG. 6A, graph 601A corresponds to the power loss at the target region (e.g., tumor) calculated based on the weighted distance between the pair of transducers on the subject's body. Graph 602A corresponds to the power loss at a tumor in the subject's head calculated based on a complex simulation calculating LMiPD. As shown in FIG. 6A, the transducer layouts identified by calculating the weighted distance using exemplary embodiments of the invention are corroborated by the complex simulations to calculate the LMiPD.

In the example depicted in FIG. 6B, graph 601B corresponds to the power loss at the target region (e.g., tumor) calculated based on weighted distance between a pair of transducers on the subject's body. Graph 602B corresponds to the power loss at a tumor in the subject's head calculated based on a complex simulation calculating LMiPD. As shown in FIG. 6B, the transducer layouts identified by calculating the weighted distance using exemplary embodiments of the invention are corroborated by the complex simulations to calculate the LMiPD.

FIGS. 7A-7D illustrate examples of the structure of various transducers. In one embodiment, the transducers comprise arrays of substantially flat electrode elements.

In FIG. 7A, the transducer 700A may have a substrate 701A and a plurality of electrode elements 702A. The substrate 701A may be configured for attaching the transducer 700A to a subject's body. Suitable materials for the substrate 701A may include, as examples, cloth, foam, and flexible plastic. In one example, the substrate 701A may include a conductive medical gel. In a more specific example, the substrate 701A may be a layer of hydrogel.

A plurality of capacitively coupled electrode elements 702A may be positioned on the substrate 701A, and each of the capacitively coupled electrode elements may have a conductive plate with a dielectric layer disposed thereon that faces towards the substrate. Optionally, one or more sensors may be positioned beneath each of the electrode elements in a manner that is similar to the conventional arrangement used in the Novocure Optune® system. In one example, the one or more sensors may be temperature sensors (e.g., thermistors).

FIG. 7B depicts another example of the structure of the transducer 700B. In this example, the transducer 700B may include a plurality of electrode elements 702B. The plurality of electrode elements 702B may be electrically and mechanically connected to one another without a substrate. In one example, the electrode elements 702B may be connected to one another through conductive wires 701B.

FIGS. 7C and 7D are further examples of the structure of the transducers 700C and 700D. For example, FIG. 7C depicts an example of a transducer 700C having an array of thirteen electrode elements 702C disposed on the substrate 701C. Furthermore, FIG. 7D depicts an example of a transducer 700D having an array of twenty electrode elements 702D disposed on the substrate 701D.

In one example, the electrode elements 702A, 702B, 702C, and 702D may be ceramic disks, and each of the ceramic disks may be approximately 2 cm in diameter and approximately 1 mm in thickness. In another example, the electrode elements 702A, 702B, 702C, and 702D may be ceramic elements that are not disk-shaped. In yet another example, the electrode elements 702A, 702B, 702C, and 702D may be non-ceramic dielectric materials positioned over a plurality of flat conductors. Examples of non-ceramic dielectric materials positioned over flat conductors may include polymer films disposed over pads on a printed circuit board or over flat pieces of metal. In particular embodiments, transducers that use an array of electrode elements that are not capacitively coupled may also be used. In this situation, each electrode element 702A, 702B, 702C, 702D may be implemented using a region of a conductive material that is configured for placement against a subject's body, with no insulating dielectric layer disposed between the conductive elements and the body. In other embodiments, the transducer may include only a single electrode element. As an example, the single electrode element may be a flexible organic material or flexible organic composite positioned on a substrate. As another example, the transducer may include a flexible organic material or flexible organic composite without a substrate.

Other alternative constructions for implementing a transducer for use with embodiments of the invention may also be used, as long as they are capable of (a) delivering TTFields to the subject's body and (b) being positioned at the locations specified herein.

FIG. 8 illustrates an example of a configuration of a pair of transducers. In this example, the first transducer 801 may include thirteen electrode elements 803 which are positioned on the substrate 804, and the electrode elements 803 may be electrically and mechanically connected to one another through a conductive wiring 809. Similarly, the second transducer 802 may include twenty electrode elements 805 which are positioned on the substrate 806, and the electrode elements 805 may similarly be electrically and mechanically connected to one another through a conductive wiring 810. Furthermore, the first transducer 801 and the second transducer 802 may be connected to an AC voltage generator 807 and a controller 808. The controller 808 may include one or more processors and memory accessible by the one or more processors. The memory may store instructions that, when executed by the one or more processors, control the AC voltage generator 807 to implement a first electric field between the first pair of transducers 801, 802, then implement a second electric field between a second pair of transducers (not shown), and then alternately iterate between implementing the first electric field and the second electric field. As shown in FIG. 8, the transducers 801, 802 are different. The transducers 801, 802 may be the same or may different in terms of, for example, number of elements and/or locations of the elements.

FIG. 9 illustrates an example of an apparatus to determine locations of transducers on a subject's body using the exemplary embodiments discussed herein. In this example, the apparatus 900 may include one or more processors 902, one or more output devices 905, and a memory 903.

In one embodiment, the one or more processors 902 may include a general purpose processor, an integrated circuit, a server, other programmable logic device, or any combination thereof. The processor may be a conventional processor, microprocessor, controller, microcontroller, or state machine. The one or more processors may be one, two, or more processors of the same or different types. Furthermore, the one or more processors may be a computer, computing device and user device, and the like.

In one example, based on user input 901, the one or more processors may determine positions at which to place transducers on a subject's body based on relationships between channels used to induce TTFields and may make one or more recommendations to the user. The one or more recommendations may be output on the one or more output devices 905. In another example, the user may give feedback regarding the one or more recommendations through the output devices 905. After receiving the feedback from the user, the one or more processors 902 may generate one or more different recommendations regarding the locations of the transducers.

The memory 903 may be accessible by the one or more processors 902 via the link 904 so that the one or more processors 902 can read information from and write information to the memory 903. Memory 903 may be integral with or separate from the processors. Examples of the memory 903 include RAM, flash, ROM, EPROM, EEPROM, registers, disk storage, or any other form of storage medium. The memory 903 may store instructions that, when executed by the one or more processors 902, implement one or more embodiments of the invention. Memory 903 may be a non-transitory computer-readable medium that stores instructions, which when executed by a computer, cause the computer to perform one or more of the exemplary methods discussed herein.

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A computer-implemented method to determine placement of transducers on a subject's body, the computer comprising one or more processors and memory accessible by the one or more processors, the memory storing instructions that when executed by the one or more processors cause the computer to perform the method, the method comprising:
   selecting a plurality of intersecting line segment pairs on an image of the subject's body, each of the line segment pairs intersecting in a region of the image corresponding to a tumor in the subject's body, each of the line segment pairs corresponding to locations to place the transducers on the subject's body;
   determining a pair value for each of the intersecting line segment pairs, each pair value based on a length of each line segment of the corresponding intersecting line segment pair, wherein determining the pair value for each of the intersecting line segment pairs comprises calculating an absolute value of a difference between lengths of the line segments of the corresponding intersecting line segment pair;
   selecting one or more intersecting line segment pairs based on the pair values to obtain one or more selected intersecting line segment pairs; and
   outputting the locations to place the transducers on the subject's body corresponding to the one or more selected intersecting line segment pairs.

2. A computer-implemented method to determine placement of transducers on a subject's body, the computer comprising one or more processors and memory accessible by the one or more processors, the memory storing instructions that when executed by the one or more processors cause the computer to perform the method, the method comprising:
   selecting a plurality of intersecting line segment pairs on an image of the subject's body, each of the line segment pairs intersecting in a region of the image corresponding to a tumor in the subject's body, each of the line segment pairs corresponding to locations to place the transducers on the subject's body, wherein the image of the subject's body includes a plurality of tissue types of the subject's body, wherein pixel tissue weightings are assigned to pixels of the image of the subject's body based on tissue types of the subject's body;
   determining a pair value for each of the intersecting line segment pairs, each pair value based on a length of each line segment of the corresponding intersecting line segment pair, wherein determining the pair value for each of the intersecting line segment pairs is based on one or more of the tissue types through which each line segment of the corresponding intersecting line segment pair passes;
   selecting one or more intersecting line segment pairs based on the pair values to obtain one or more selected intersecting line segment pairs; and
   outputting the locations to place the transducers on the subject's body corresponding to the one or more selected intersecting line segment pairs.

3. The computer-implemented method of claim 1, wherein determining the pair value for each of the intersecting line segment pairs comprises:
   identifying pixels of the image with which each line segment of each of the intersecting line segment pairs intersects; and
   determining the pair value based on the pixels intersecting each line segment of the intersecting line segment pair.

4. The computer-implemented method of claim 3, wherein pixel tissue values are assigned to pixels of the image based on tissue types of the subject's body, and
   wherein determining the pair value for each of the intersecting line segment pairs further comprises:
      determining the pair value based on the pixel tissue values for the pixels intersecting each line segment of the intersecting line segment pair.

5. The computer-implemented method of claim 1, wherein the line segments of the intersecting line segment pairs intersect at a point within the tumor in the image, at a centroid of the tumor in the image, or at a point adjacent to the tumor in the image.

6. The computer-implemented method of claim 1, wherein the line segments of at least one of the intersecting line segment pairs are substantially perpendicular.

7. The computer-implemented method of claim 1, wherein a first line segment of a first intersecting line segment pair is spaced apart by a predetermined angle from a first line segment of a second intersecting line segment pair; and
   wherein a first line segment of the second intersecting line segment pair is spaced apart by the predetermined angle from a first line segment of a third intersecting line segment pair.

8. The method of claim 1, wherein at least one of the one or more selected intersecting line segment pairs has a local minimum power density (LMiPD) at an intersection of the line segments higher than an LMiPD at an intersection of the line segments of non-selected intersecting line segment pairs.

9. The computer-implemented method of claim 1, wherein the transducers comprise arrays of substantially flat electrode elements.

10. The computer-implemented method of claim 1, wherein the one or more selected intersecting line segment pairs are selected without simulating TTFields for transducer locations on the subject's body.

11. The computer-implemented method of claim 1, wherein the locations to place the transducers on the subject's body are outputted without simulating the TTFields for the locations.

12. The computer-implemented method of claim 2, wherein determining the pair value for each of the intersecting line segment pairs comprises calculating a summation of lengths of the line segments of the corresponding intersecting line segment pair.

13. The computer-implemented method of claim 2, wherein the tissue types of the subject's body comprise gray matter, white matter, and bone.

14. The computer-implemented method of claim 2, wherein the tissue types of the subject's body comprise organ tissue, muscular tissue, and bone.

15. The computer-implemented method of claim 2, wherein determining the pair value for each of the intersecting line segment pairs comprises calculating an absolute value of a difference between lengths of the line segments of the corresponding intersecting line segment pair.

16. A non-transitory computer-readable medium comprising instructions to identify locations to place transducers on a subject's body, the instructions when executed by a computer cause the computer to perform a method comprising:
   selecting a plurality of intersecting line segment pairs on an image of the subject's body, each of the line segment pairs intersecting in a region of the image corresponding to a tumor in the subject's body, each of the line segment pairs corresponding to locations to place the transducers on the subject's body;
   determining a pair value for each of the intersecting line segment pairs, each pair value based on a number of pixels in the image of the subject's body through which the line segment pairs pass, wherein determining the pair value for each of the intersecting line segment pairs comprises calculating an absolute value of a difference between the number of pixels of the line segments of the corresponding intersecting line segment pair;
   selecting one or more intersecting line segment pairs based on the pair values to obtain one or more selected intersecting line segment pairs; and
   outputting the locations to place the transducers on the subject's body corresponding to the one or more selected intersecting line segment pairs.

17. The method of claim 16, wherein pixel tissue values are assigned to pixels of the image based on tissue types of the subject's body, and
   wherein determining the pair value for each of the intersecting line segment pairs is further based on the pixel tissue values of pixels in the image of the subject's body through which the line segment pairs pass.

18. A system to identify locations to place transducers on a subject's body, the system comprising one or more processors and memory accessible by the one or more processors, the memory storing instructions that when executed by the one or more processors cause the system to perform a method comprising:
   accessing an image of a slice of the subject's body, the image including a region associated with a tumor of the subject's body, the tissue types of the subject's body identified in the image;
   selecting a plurality of intersecting line segment pairs on the image of the slice of the subject's body, each of the line segment pairs intersecting in a location of the image corresponding to the tumor of the subject's body, each line segment of the plurality of line segment pairs has a first endpoint and a second endpoint on a surface of the subject's body;
   determining a pair value for each of the intersecting line segment pairs, each pair value based on a weighted distance between the first endpoint and the second endpoint of each line segment of the corresponding intersecting line segment pair, wherein determining the pair value for each of the intersecting line segment pairs further comprises calculating an absolute value of a difference between the weighted distance of the line segments of the corresponding intersecting line segment pair;
   selecting one or more intersecting line segment pairs based on the pair values to obtain one or more selected intersecting line segment pairs; and
   outputting the pair values for the one or more selected intersecting line segment pairs, wherein the one or more selected intersecting line segment pairs correspond to locations to place the transducers on the subject's body.

19. The system of claim 18, wherein the weighted distance between the first endpoint and the second endpoint of each line segment is based on one or more tissue types within the subject's body through which the corresponding line segment passes.

* * * * *